(12) United States Patent
Yellepeddi et al.

(10) Patent No.: US 7,983,386 B2
(45) Date of Patent: Jul. 19, 2011

(54) X-RAY ANALYSIS INSTRUMENT

(75) Inventors: Ravisekhar Yellepeddi, Chavornay (CH); Pierre-Yves Negro, Ecublens (CH); Michel Bonzon, Epalinges (CH)

(73) Assignee: Thermo Fisher Scientific, Inc., Waltham, MA (US)

( * ) Notice: Subject to any disclaimer, the term of this patent is extended or adjusted under 35 U.S.C. 154(b) by 18 days.

(21) Appl. No.: 12/529,114

(22) PCT Filed: Feb. 28, 2008

(86) PCT No.: PCT/EP2008/001566
§ 371 (c)(1),
(2), (4) Date: Aug. 28, 2009

(87) PCT Pub. No.: WO2008/107108
PCT Pub. Date: Sep. 12, 2008

(65) Prior Publication Data
US 2010/0111251 A1    May 6, 2010

(30) Foreign Application Priority Data

Mar. 6, 2007 (GB) .................................. 0704322.7

(51) Int. Cl.
*G01N 23/223* (2006.01)

(52) U.S. Cl. .......................................... 378/44; 378/70
(58) Field of Classification Search ............. 378/44–50, 378/70, 73, 79, 80, 82
See application file for complete search history.

(56) References Cited

U.S. PATENT DOCUMENTS

2006/0088139 A1\* 4/2006 Nakano et al. .................. 378/79
\* cited by examiner

*Primary Examiner* — Hoon Song
(74) *Attorney, Agent, or Firm* — Charles B. Katz

(57) ABSTRACT

An apparatus for carrying out both x-ray diffraction (XRD) and x-ray fluorescence (XRF) analysis of a crystalline sample. A sample holder is located within an evacuable chamber. An x-ray fluorescence source and separate x-ray diffraction source are mounted within the evacuable chamber. An XRF detection arrangement is also provided, for detecting secondary x-rays emitted from the surface of the crystalline sample as a result of illumination by x-rays from the said x-ray fluorescence source. An XRD detection arrangement is then provided for detecting x-rays of a characteristic wavelength which have been diffracted by the crystalline sample. A moveable XRD support assembly is provided, comprising a first part configured to mount the XRD source for relative movement between the XRD source and the sample holder, and a second part configured to mount the XRD detection arrangement for relative movement between the XRD detection arrangement and the sample holder.

13 Claims, 4 Drawing Sheets

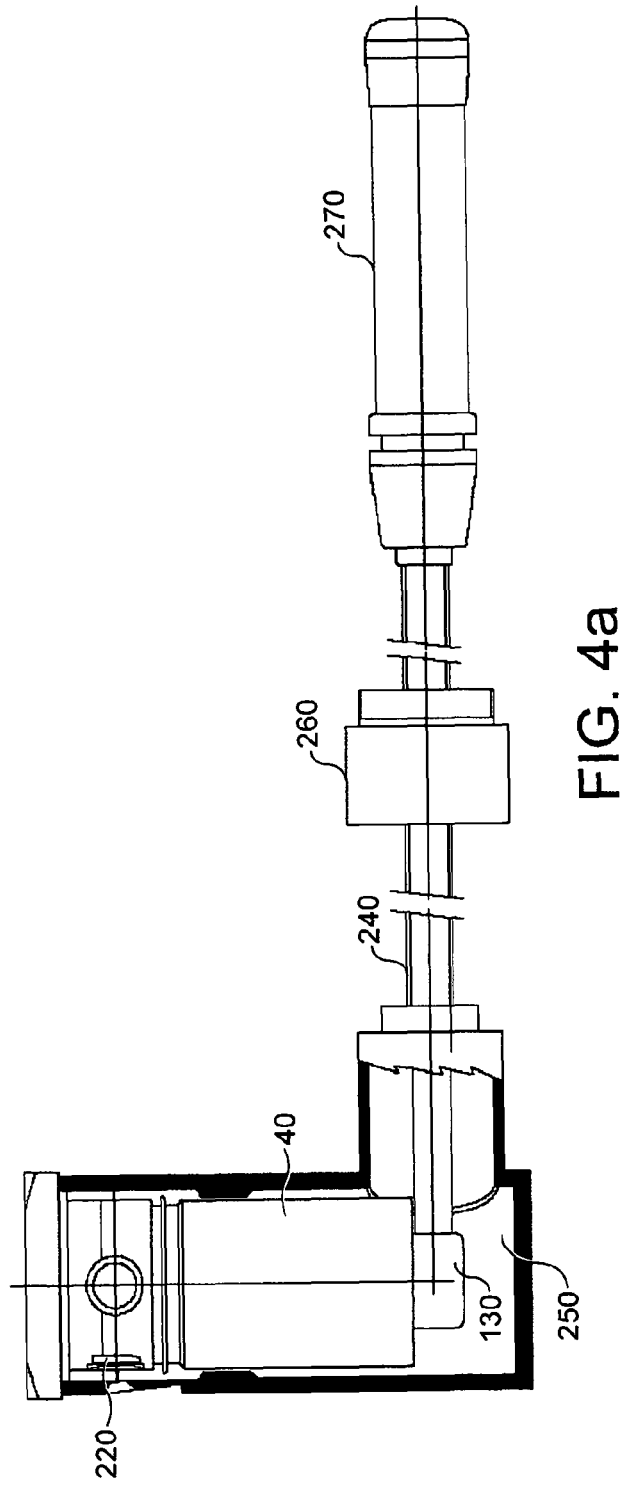
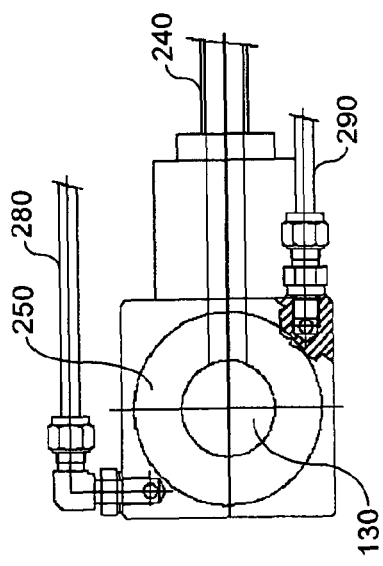
FIG. 4a
FIG. 4b

X-RAY ANALYSIS INSTRUMENT

FIELD OF THE INVENTION

This invention relates to an X-ray analysis instrument for carrying out elemental and crystallographic analysis in a sample.

BACKGROUND OF THE INVENTION

A variety of techniques are established in the art for analysing both the elemental and structural characteristics of a material having a crystalline structure. For example, x-ray diffraction (XRD) relies upon analysis of the pattern produced by diffraction of x-rays through the closely spaced lattice of atoms in a crystal to reveal the structural constituency of the analysed material. Bragg's law allows the spacing in the crystal lattice to be inferred from the measured path difference for diffracted x-rays.

X-Ray fluorescence (XRF), by contrast, is a spectroscopic technique to allow elemental investigation of a sample without the need for chemical analysis. In XRF, illumination of a sample with an x-ray beam results in emission of secondary x-rays having characteristic wavelengths which are indicative of the elemental constituency of the sample. In order to permit multi elemental analysis, the x-ray source for XRF is typically polychromatic.

Combined XRD/XRF instruments have existed for many years. A first type of combined XRD/XRF instrument operates with the sample at atmospheric pressure. A second type of combined instrument operates in vacuo. Each type has advantages and disadvantages: instruments wherein the sample is analysed in a vacuum tend to provide an enhanced x-ray analysis particularly though not exclusively for XRF where the sensitivity to elements having a low atomic number is increased. On the other hand, the size and physical arrangement of a non-vacuum instrument is less constrained, and moreover changing of samples can be carried out more promptly.

For high quality XRD and a more complete structural characterisation for mineralogy and phase analysis, it is desirable to be able to change the measurable angle of diffraction through a wide range. In a non-vacuum system this does not present too much difficulty. However in a vacuum chamber the restricted space limits the opportunity to improve performance.

Several solutions to the problem of limited space when analysing a sample in a vacuum chamber using XRD techniques are proposed in the art.

In XRD-only devices, the x-ray tube and detector may be rotated with the sample fixed. For combined XRD/XRF devices however, a single x-ray tube is held in a fixed location relative to the vacuum chamber and the sample is rotated whilst the detector is held fixed, the sample is held fixed whilst the detector is rotated, or, as in U.S. Pat. No. 4,263,510, U.S. Pat. No. 5,369,275 and U.S. Pat. No. 4,916,720, the sample and detector are both rotated. The latter arrangement appears to provide the highest performance in vacuo.

For high quality XRF, however, the distance between the sample and the tube needs to be small. Unfortunately this requirement forces a compromise in a combined XRD/XRF instrument since, as noted, the highest quality XRD measurements require the sample to be rotatable. This in turn puts a minimum distance requirement on the location of the x-ray tube relative to the sample (to avoid collisions between the two during XRD measurements), so reducing the maximum performance during XRF measurements.

Commonly assigned U.S. Pat. No. 5,406,608 describes a combined XRD/XRF analyser for analysing samples in vacuo. An x-ray source is mounted in fixed relation to a vacuum chamber of the instrument and provides a polychromatic divergent x-ray beam which illuminates a sample to permit both XRD and XRF measurements. One or more fixed and/or moveable fluorescence channels are provided so as to allow selection of x-rays of a particular wavelength and energy, and to detect the selected x-ray. A diffraction channel is also provided which allows selection of a characteristic x-ray wavelength at the source following diffraction by the sample. The diffraction channel also has a detection arrangement. The x-ray diffraction detector is rotatable to improve XRD measurements. XRF performance is however optimised by providing multiple fluorescence channels or by mounting a fluorescence channel (incorporating a detection arrangement) on a goniometer rotatable about the sample.

Whilst the foregoing arrangement provides a fair compromise between XRD and XRF performance, it does however suffer from a number of drawbacks. Firstly, the sample is fixed relative to the x-ray tube (in other words only the XRD detector arrangement is rotatable, not the sample) which limits XRD performance. Secondly, in seeking to avoid compromising the XRF performance, the arrangement of tube, sample detectors and vacuum chamber in U.S. Pat. No. 5,406,608 restricts the angular range of the XRD detector which in turn limits the ability to perform more extensive XRD measurements.

SUMMARY OF THE INVENTION

Against the foregoing background, it is an object of the present invention to provide an improved XRD/XRF analysis instrument for analysis of samples in vacuo. According to the present invention there is provided an apparatus for carrying out both x-ray diffraction (XRD) and x-ray fluorescence (XRF) analysis of a crystalline sample, comprising: an evacuable chamber; a sample holder located within the evacuable chamber, for mounting the crystalline sample so that it may be analysed; an x-ray fluorescence source mounted within the evacuable chamber, for illuminating the crystalline sample with x-rays; an XRF detection arrangement for detecting secondary x-rays emitted from the surface of the crystalline sample as a result of illumination by x-rays from the said x-ray fluorescence source; characterized by an x-ray diffraction source, also mounted within the evacuable chamber but separate from the x-ray fluorescence source, for illuminating the crystalline sample with x-rays; an XRD detection arrangement for detecting x-rays of a characteristic wavelength which have been diffracted by the crystalline sample; and a moveable XRD support assembly, comprising a first part configured to mount the XRD source for relative movement between the XRD source and the sample holder, and a second part configured to mount the XRD detection arrangement for relative movement between the XRD detection arrangement and the sample holder. The apparatus in accordance with the invention thus provides separate x-ray tubes within the vacuum chamber, a first for illuminating the sample with x-rays for XRF and a second for illuminating the sample with x-rays for XRD. The XRD tube and the corresponding XRD detection arrangement are both mounted for relative movement with respect to the sample. The apparatus is therefore capable of acquiring XRF data for complete chemical or elemental analysis while the XRD data provide the complete structural or phase analysis on the same sample within the same embodiment under vacuum.

Previous combined XRD and XRF arrangements have either compromised on accuracy and/or ability to measure low atomic number elements by having the sample at atmosphere, or have used a single static x-ray tube in vacuo, for both XRD and XRF. The latter arrangements result in compromises: either the range of angles of XRD measurements is limited (for example, where the XRD detector is moveable as in the arrangement of U.S. Pat. No. 5,406,608, the range of available angles is between about 25 and 55 degrees), and/or the proximity of the x-ray source to the sample, for XRF measurements is limited, since the requirement to rotate the sample forces the x-ray tube to be backed off from the sample (to prevent collisions) which limits XRF performance.

It is well known by those skilled in the art that increasing the number of x-ray tubes is difficult in a vacuum chamber because of the additional cooling requirements. For accurate XRD measurements, an x-ray source of 1 kW or more is recommended; the preferred embodiment is a 1.8 kW source operating at 45 kV and 40 mA. Mounting a powerful x-ray source within vacuum complicates the problem of cooling the source as the available surface area through which heat can be transferred is reduced. It is therefore desirable to mount as much of the x-ray tube outside the vacuum chamber as possible to allow heat transfer out of the tube. However for a combined XRD-XRF instrument, the XRD detector must be mounted on the same side of the sample as is the tube, and must be displaced away from the sample. This displacement is required so that diffracted x-rays have diverged before reaching the detector so that the detector can have improved angular resolution. The distance between the sample and the detector should be maintained under vacuum and so the sample must be well inside the vacuum chamber. This then means that a fixed x-ray tube must also protrude deep inside the vacuum chamber and only one end of the x-ray tube is accessible from outside the vacuum chamber, exacerbating the heat transfer problem. This problem is further compounded if that x-ray tube must be rotatable within vacuum as there then cannot be any part of the tube that abuts the housing, and the tube is fully enclosed within vacuum. Previous combined XRD-XRF instruments have been restricted either by using the same fixed x-ray tube for both XRD and XRF, or by using two fixed x-ray tubes and rotating the sample and the XRD detector when performing XRD analysis.

Additionally, increasing the number of x-ray sources requires increased space within the vacuum chamber. Space is at a premium in a vacuum chamber because increasing the size of the vacuum chamber increases its manufacturing cost and requires larger capacity, more expensive, vacuum pumps. Furthermore, as U.S. Pat. No. 5,406,608 and other prior art documents also acknowledge, a single x-ray source minimizes cost.

However, the inventors have realised that, if a second tube is provided for XRD, which is moveable relative to the sample and a moveable XRD detection arrangement is provided as well, a much wider range of diffraction angles can be measured. Preferred embodiments permit a range of a few degrees (eg, 7 degrees) up to about 80 degrees to be measured. At the same time the separate XRD tube and detection arrangement avoids the need to compromise with XRF, so that, in preferred embodiments the (separate) XRF tube can be mounted in fixed, close proximity to the sample in the sample holder (which may, nonetheless, be journalled for rotation about a vertical axis).

By having the XRD apparatus in vacuo, the sample can be isolated from, for example, moisture ingress. This in turn assists in the analysis of certain industrial compounds such as cement and its constituents (eg, free lime) which are very hygroscopic and thus rapidly deteriorate in the presence of water in moist air.

By having the sample fixed horizontally, powder samples can be accommodated without spillage. Prior art configurations where the sample holder rotates are either limited in the types of samples that they can analyse, or must restrict the sample angle rotation, limiting the performance of the XRD measurements able to be made. Powder samples are commonly analysed in the cement industry, for example.

Preferably the XRD tube and XRD detection arrangement are each mounted upon separate arms of a single goniometer. Alternatively, two separate goniometers may be utilised so that the motions of the XRD source and XRD detector may be operated independently, though it is preferable that both motions be controlled by a single controller such as a computer. The XRD tube is preferably located wholly within the vacuum chamber so that its angular motion is unrestricted, and in that case the appropriate power and cooling facilities may be provided by employing high vacuum feed-throughs from external of the vacuum chamber into the interior thereof, with, optionally, flexible conduits within the chamber so that the XRD tube may move relative to the chamber.

A significant advantage of such a fully integrated XRD and XRF apparatus is the synergy of chemical analysis data to interpret the XRD data for mineral analysis in that the XRF data is provided as additional input to the XRD processing system in order to validate and quantify the corresponding minerals or phases in the same sample. A single operating system preferably collects the data from both XRF and XRD modes of the instrument which is then processed to obtain a complete chemical and mineral characterization of the polycrystalline material.

BRIEF DESCRIPTION OF THE DRAWINGS

The invention may be put into practice in a number of ways, and a specific embodiment will now be described by way of example only and with reference to the accompanying figures in which:

FIG. 4*a* shows a sectional view along the line C-C' of FIG. 1, illustrating the XRD tube in further detail together with its manner of connection with and through the vacuum housing; and FIG. 4*b* shows a side view of the arrangement of FIG. 4*a*.

DETAILED DESCRIPTION OF A PREFERRED EMBODIMENT

Figure 1:
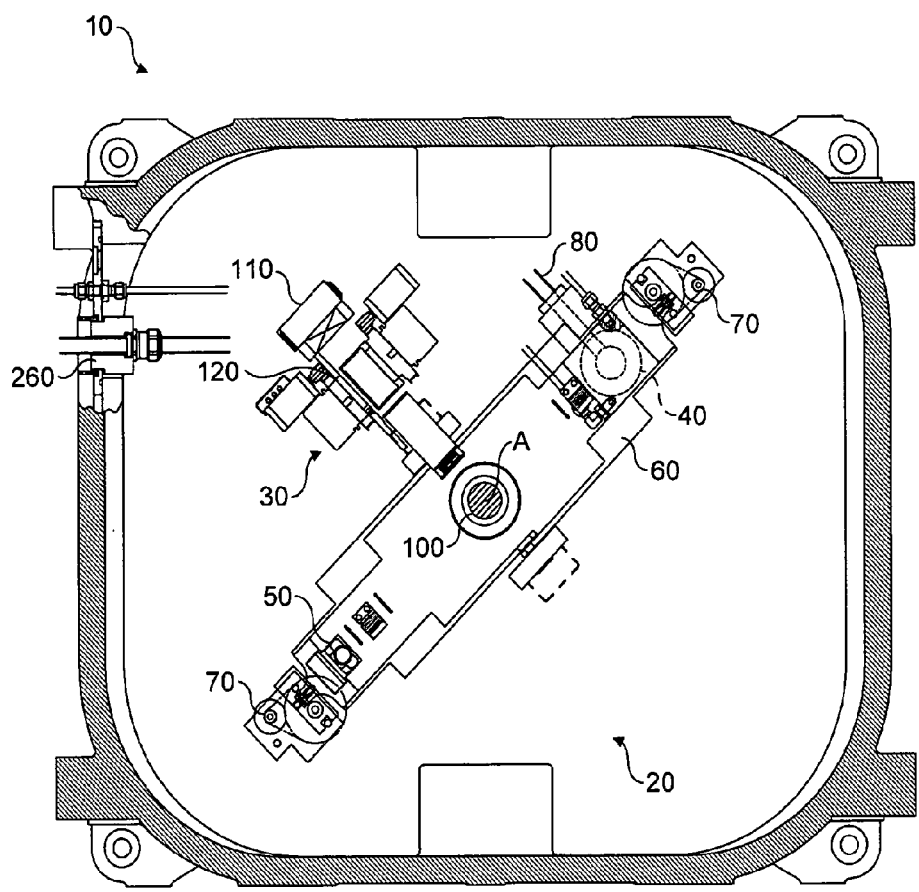
FIG. 1 shows a top view of a combined XRD/XRF apparatus embodying the present invention and including both XRD and XRF tubes and detectors.

Referring first to FIG. 1, a schematic top view of a combined XRD/XRF apparatus 10 is shown. The apparatus 10 includes a vacuum chamber 15 containing XRD components, labelled generally at 20, and described in further detail below as well as in connection with FIG. 2, and separate XRF components indicated generally at 30 and described below in connection with FIG. 3.

The XRD components 20, in more detail, comprise an XRD tube 40 and an XRD detector 50, each of which is mounted upon a respective arm of an XRD goniometer 60. The goniometer 60 and the XRD tube 40 and XRD detector 50 mounted upon it are moveable relative to a vertical axis A (passing into the paper as viewed in FIG. 1) in a manner to be described subsequently. The axis A also defines the centre of a sample holder 100 which, in use, holds a crystalline sample (not shown) to be analysed.

Associated with the XRD goniometer 60 are goniometer drivers 70 which may, for example, be manually or computer controlled to drive the XRD goniometer 60 to a chosen angular position. Finally, FIG. 1 also illustrates schematically the location of cooling and power conduits 80, for providing cooling and electrical power to the XRD tube 40. As may be seen from the plan view of FIG. 1, the XRD tube 40 is physically isolated from the walls of the vacuum chamber 15 so its motion may be unimpeded. The vacuum chamber 15 itself is, in use, evacuated using standard pumping equipment which will be familiar to those of ordinary skill and which is not illustrated in FIG. 1.

The separate XRF components 30 comprise, in brief, an XRF tube 90 which is fixed relative to the sample holder 100 and the vacuum chamber 15, and is located coaxially with the axis A of the sample holder 100. The XRF components 30 also include an XRF detector 110 mounted upon an XRF goniometer 120. Instead of a single XRF detector 110 mounted upon an XRF goniometer 120 so that the detector 110 may be moved, a plurality of fixed XRF channels may instead be located at spatially separate places within the vacuum chamber 15, to allow simultaneous selection and measurement of fluorescence x-rays from the sample of differing energies. The details of the XRF detector do not, however, form a part of the present invention and any suitable known arrangement may be employed, such as that which is described in detail in commonly assigned U.S. Pat. No. 5,406,608, the contents of which are incorporated by reference in their entirety.

Figure 2:
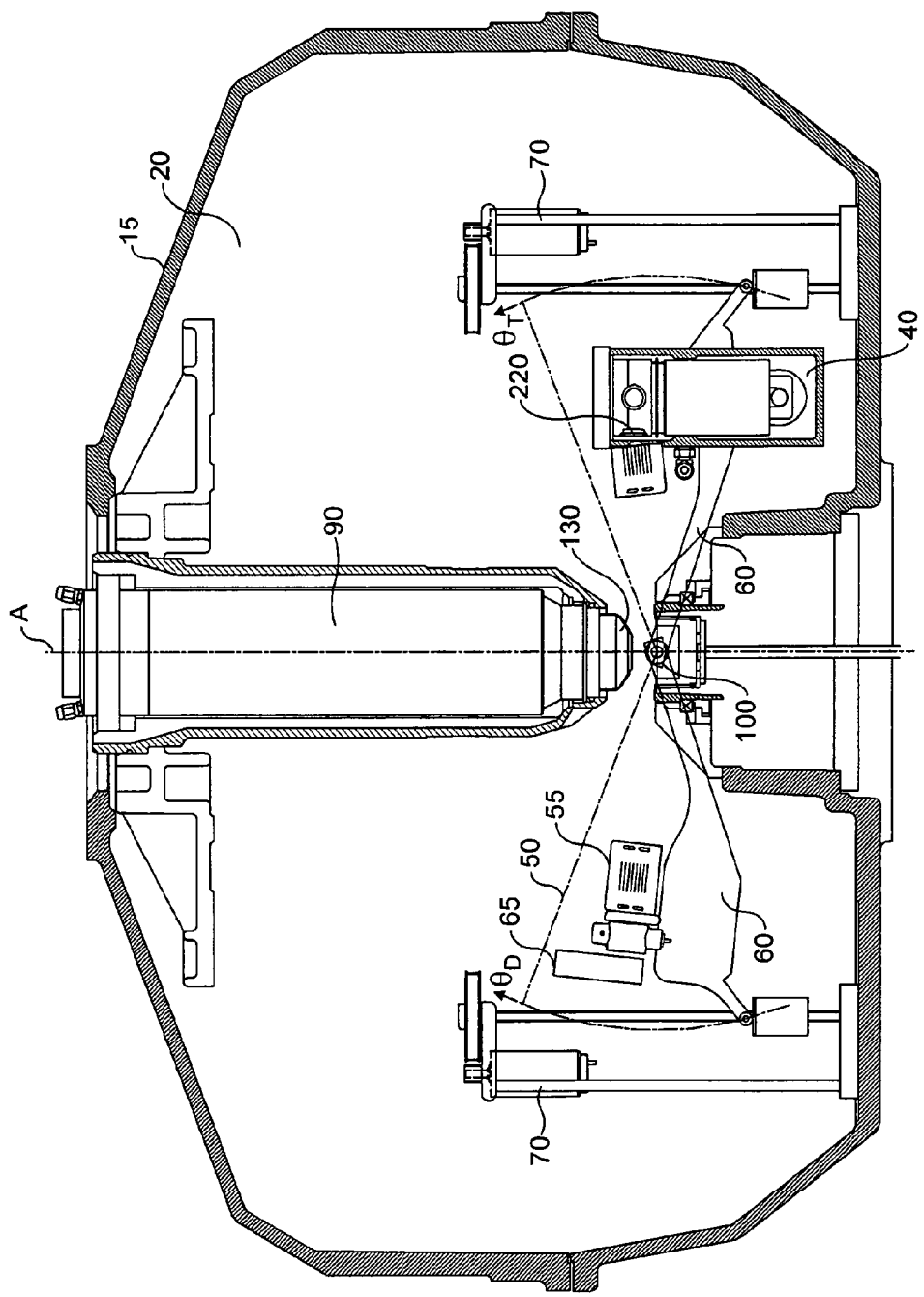
FIG. 2 shows a sectional view along a line A-A' of FIG. 1, further illustrating the arrangement of the XRD tube and detector.

FIG. 2 shows a sectional view along the line A-A' of FIG. 1, illustrating the arrangement of the XRD components 20 in further detail. As described above in connection with FIG. 1, a vertical axis A defines a longitudinal axis of the XRF tube 90 which has a rhodium tipped anode 130 located adjacent the sample holder 100. The use of rhodium as an x-ray anode target material is, of course, merely one of a range of possible target materials, such as copper, tungsten, molybdenum and gold; the specific target material of the x-ray anode which is employed determines the energy distribution of the x-rays emitted from the XRF tube 90.

As may be seen more clearly in FIG. 2, the axis of the sample holder 100 is coterminous with the axis A of the XRF tube 90.

The XRD tube 40 is mounted upon the right hand arm of the XRD goniometer 60 as viewed in FIG. 2. The XRD tube 40 is preferably a monochromatic source of x-rays which allows a well resolved diffraction pattern to be obtained, as described below. The XRD tube 40 also preferably has a relatively high power output in order to provide for the lowest detection limits. In the preferred embodiment, the power output of the XRD tube 40 is 1800 Watts at 45 kV and 40 mA.

The XRD tube 40 has a tube window 220 (see also FIG. 4a) which communicates with XRD divergent optics 45 on the output thereof, to produce a divergent, monochromatic beam of x-rays that that irradiates the sample in the sample holder 100.

In use, the right hand goniometer driver 70 actuates the right hand arm of the XRD goniometer 60 so that the XRD tube 40 describes arcuate movement about the sample holder 100 wherein a sample is mounted. The general direction of movement of the XRD tube on the goniometer arm is indicated by $\theta_D$. The angle between the sample (strictly, the crystal plans within the sample) and the XRD tube defines the diffraction in accordance with Braggs's Law: $n\lambda = 2d_{hkl} \sin\theta_1$ where n is an integral number of wavelengths $\lambda$, $\theta_1$ is the angle of diffraction, and $d_{hkl}$ is the interplanar distance dependent upon the Miller indices h, k and l of the crystal. The Bragg Law requirement that $\theta$ and $\lambda$ are matched necessitates that a range of wavelengths or angle is available. The wider the range of angles $\theta$ is available, the more information on the crystal structure may be obtained.

Mounted on the left hand arm (as viewed in FIG. 2) of the XRD goniometer 60 is an XRD detector 50. As with the XRD tube 40, the goniometer driver 70 allows the left hand XRD goniometer arm to drive the XRD detector 50 in an arcuate direction $\theta_D$ about the sample holder 100. The details of the XRD detector 50 do not form a part of the present invention as such and the skilled person will appreciate that any suitable XRD detection arrangement could be employed. In brief, however, the XRD detector comprises XRD receiving optics 55 including a monochromator crystal, a collimator (not shown) and a detector array 65. The monochromator crystal is positioned at a specific angle relative to the sample and the diffracted beam, such that a chosen characteristic wavelength from the XRD source 40 is selected and passes into the detector. When the apparatus 10 embodying the present invention is operated in combined XRD/XRF mode (that is, with both XRD and XRF analyses taking place simultaneously), this crystal isolates fluorescence x-rays from the XRF tube 90 (which can cause a huge background in XRD analysis), and also unwanted diffraction peaks, so that a diffraction pattern of the sample may be obtained by scanning of the XRD tube 40 and XRD detector 50. It is to be understood that the monochromator is not an essential feature of the XRD detector, however. For example, the primary radiation from the XRD tube 40 could be filtered instead so as to provide a single wavelength beam (e.g., the Copper K alpha line). In that case the monochromator can be omitted from the secondary beam particularly where the XRF tube 90 is not operating simultaneously (so that the problems of sample fluorescence creating a background during XRD analysis are avoided).

In one embodiment the XRD tube 40 and XRD detector 50 are independently moveable via the goniometer drivers 70, but in a preferred embodiment a central controller governs arcuate movement of both so that a wide range of angles between the x-ray source from XRD tube 40 and the detection channel in the detector 50 can be achieved. Importantly, because the XRD and XRF components 20, 30 are in different planes (along different axes—see FIG. 1), with separate x-ray tubes for each part of the system, there is significantly more room for movement of the XRD tube 40 and XRD detector 50, resulting in a total angle subtended between the source of x-rays from the XRD tube 40 and the XRD detector 50 down to around 7 degrees (approximately 3.5 degrees to the horizontal, on each side of the sample), up to as much as 80 degrees (40 degrees to the horizontal for the XRD tube 40 and XRD detector 50 respectively).

Photons detected by the XRD detector 50 are counted and processed by electronic means which is not shown, to provide a diffractogram.

Figure 3:
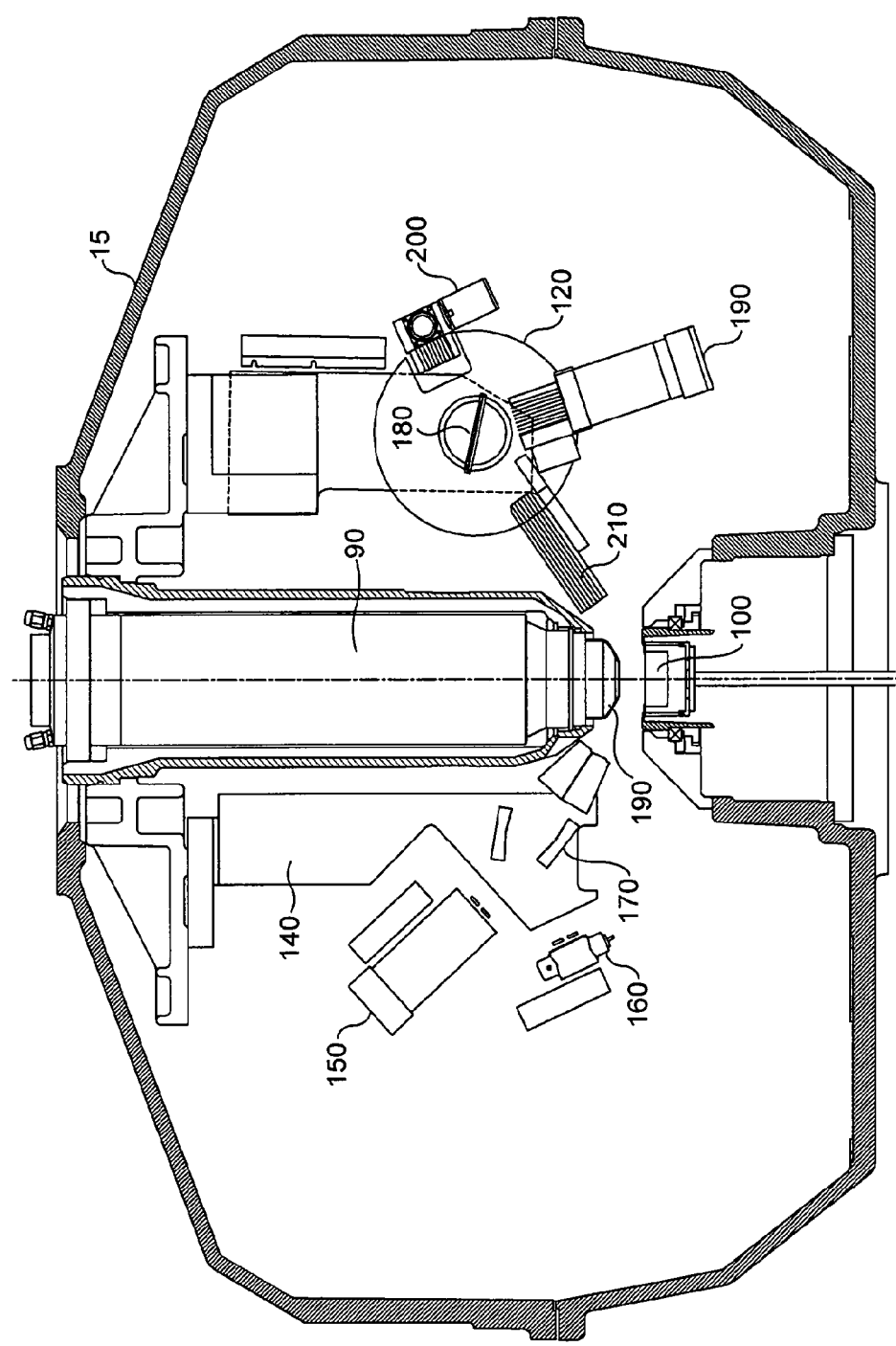
FIG. 3 shows a sectional view along the line B-B' of FIG. 1, further illustrating the arrangement of the XRF tube and detectors.

Turning now to FIG. 3, a section along the line B-B' of FIG. 1 is shown. Again the XRF tube 90 is shown along the longitudinal axis A with the anode 130 shown adjacent to the sample in the sample holder 100.

In use, x-rays from the XRF tube 90 strike the sample in the sample holder 100 and this causes the emission of secondary x-rays. The sample holder 100 is itself rotatable to permit the sample orientation to be altered during investigation. Characteristic energies of fluorescence x-rays emitted from the sample are separated from the continuum of x-ray energies by, for example, Bragg reflection from the surface of a crystal. A static fluorescence detection channel operable on this basis is shown on the left hand side of FIG. 3. The static fluorescence detection channel comprises an XRF monochromator 140, an XRF scintillation detector 150, an XRF sealed or gas flow detector 160 such as a gas filled counter, and an XRF Bragg crystal 170.

Fluorescence x-rays from the sample pass into the monochromator 140 and impinge on the Bragg crystal 170 which diffracts only one wavelength related to a specific element at a particular Bragg angle. The Bragg crystal 170 thus acts to monochromate and focus a beam of x-rays of the desired energy onto the detectors 150, 160. A number of static fluorescence channels such as that shown in the left hand side of FIG. 3 may be employed to allow simultaneous selection and measurement of fluorescence x-rays of differing energies. Such an array of static channels is particularly useful when the apparatus 10 is set up to monitor, for example, the specific proportions of known elements within an industrial process such as the manufacture of steel or cement.

The use of static fluorescence channels is, however, typically otherwise inflexible since each channel is configured to measure only a certainly energy (and hence, to identify a specific element). To overcome this drawback, therefore, a sequential fluorescence channel mounted upon an XRF goniometer 120 may additional or alternatively be provided and such an arrangement is shown on the right hand side of FIG. 3. The XRF detector 110 of FIG. 1 is shown in more detail as, for example, a scintillation detector 190 and a flow proportional counter (FPC) detector 200. Each is mounted upon the XRF goniometer 120 along with a collimator 210. The XRF goniometer 120 is based upon a $\theta$-$2\theta$ rotation wherein a fluorescence spectrum with multiple wavelengths is collimated by a primary collimator in front of a flat crystal monochromator. The crystal diffracts only one wavelength pertaining to one specific element of interest at a given angle. This diffracted wavelength is then further collimated by a secondary collimator in front of the detector. The crystal is positioned at an angle $\theta$ and the detector is located at an angle $2\theta$ by means of an optical encoder mechanism. As the crystal is rotated, that is, as the angle $\theta$ is changed, different wavelengths are diffracted at different angles and are identified by the detector moving in synchronisation at an angle of $2\theta$. In this manner, a complete spectrum may be obtained. By contrast a fixed XRF channel is designed for one specific wavelength in a static measurement. In other words, the XRF goniometer 120 acts as a sequential system wherein one wavelength at a time is measured during a scan. The monochromator or fixed XRF channel is on the other hand pre-aligned with a fixed crystal and fixed detector positions to pick up one specific wavelength. Preferred embodiments of the present invention allow for both an XRF goniometer 120 for flexible, sequential XRF measurements along with a plurality of fixed XRF channels for specific measurement/detection of a finite range of known elements (as well, of course, as the separate XRD components 20).

Turning finally to FIG. 4a, a section along the line C-C' of FIG. 1 is shown, though not to scale. FIG. 4a shows a partial side and cutaway section of the XRD tube 40 along with associated cooling and power connections. As is apparent from FIG. 1 and the foregoing description, the XRD tube 40 is mechanically and thermally isolated from the vacuum chamber 15 (unlike the XRF tube 90 which is suspended from the top of it). By isolating the XRD tube 40 from the vacuum chamber 15, the former is capable of movement relative to the latter. The isolation of the XRD tube 40 from the vacuum chamber 15 also prevents thermal conduction, that is, prevents the vacuum chamber 15 from acting as a heat sink for the XRD tube 40. As such, however, it is desirable alternatively to cool the XRD tube 40. It is also necessary to supply power at relatively high voltages to the XRD tube 40 and the arrangement of FIG. 4a suggests one embodiment for doing this. As seen in FIG. 4a, and also in FIG. 4b which is a close up plan view of the XRD tube 40 as first shown in FIG. 1, a high vacuum connection 230 to the XRD tube 40 is provided at an end thereof. A high voltage cable 240 extends transversely from this high vacuum connection 230 from the XRD tube 40 towards the vacuum chamber wall. The high vacuum connection and the cable as it extends from that are potted using an electrically insulating material such as an epoxy resin which may be doped with thermal conductor to assist with the cooling of the x-ray tube 40.

An insulating stand off or flange 260 within the wall of the vacuum chamber 15 provides electrical isolation between the inside of the vacuum chamber 15 and atmosphere whilst at the same time providing a vacuum tight seal. On the atmosphere side of the vacuum chamber 15, a second high voltage connection 270 to an external power supply (not shown) is provided.

Finally, water cooling to the x-ray tube is effected by a water cooling inlet 280 and a water cooling outlet 290. Both inlet and outlet are formed of pipes or conduits which are at least partly flexible to allow movement of the XRD tube 40 relative to the vacuum chamber 15. Although not shown in FIG. 4a or 4b, vacuum tight feed throughs or flanges are also provided in the walls of the vacuum chamber 15 to allow connection of an external water supply.

Although one specific embodiment of the present invention has been described for illustrative purposes only, the skilled person will understand that various modifications may be contemplated without departing from the scope of the invention which is defined in the accompanying claims.

The invention claimed is:

1. An apparatus for carrying out both x-ray diffraction (XRD) and x-ray fluorescence (XRF) analysis of a crystalline sample, comprising:
   an evacuable chamber;
   a sample holder located within the evacuable chamber, for mounting the crystalline sample so that it may be analysed;
   an XRF tube mounted within the evacuable chamber, for illuminating the crystalline sample with x-rays;
   an XRF detection arrangement for detecting secondary x-rays emitted from the surface of the crystalline sample as a result of illumination by x-rays from the XRF tube;
   an XRD tube mounted within the evacuable chamber separately from the XRF tube, for illuminating the crystalline sample with x-rays;
   an XRD detection arrangement for detecting x-rays of a characteristic wavelength which have been diffracted by the crystalline sample; and
   a moveable XRD support assembly, comprising a first part configured to mount the XRD tube for relative movement between the XRD tube and the sample holder, and a second part configured to mount the XRD detection arrangement for relative movement between the XRD detection arrangement and the sample holder;
   wherein the XRD tube is movable relative to the sample holder without affecting the position of the XRF tube.

2. The apparatus of claim 1, wherein the first part of the moveable support assembly is configured to mount the XRD tube for rotatable movement through a plurality of angular positions relative to the sample holder, and wherein the second part of the moveable support assembly is configured to mount the XRD detector for rotatable movement through a plurality of angular positions relative to the sample holder.

3. The apparatus of claim 2, wherein the moveable support assembly comprises a goniometer, the first part of the moveable support assembly including a first arm of the goniometer and the second part of the moveable support assembly including a second arm of the goniometer.

4. The apparatus of claim 3, further comprising goniometer actuating means for actuating each of the first and second goniometer arms so as to control arcuate movement of the XRD tube and XRD detection arrangement, respectively, about the sample holder, between first and second end stop positions.

5. The apparatus of claim 4, wherein the sample holder defines a horizontal plane within the evacuable chamber, wherein the first and second end stop positions of the XRD detection arrangement subtend angles of approximately 3 degrees and 40 degrees to that horizontal plane respectively, and wherein the first and second end stop positions of the XRD tube subtend angles of approximately 3 degrees and 40 degrees to that horizontal plane respectively.

6. The apparatus of claim 1, wherein the XRF tube is mounted in a fixed position relative to the sample holder and the evacuable chamber.

7. The apparatus of claim 6, wherein the XRF tube has a longitudinal axis which intersects the sample holder.

8. The apparatus of claim 1, wherein the sample holder is rotatable about an axis.

9. The apparatus of claim 1, wherein the XRF detection arrangement is mounted upon a moveable XRF support assembly.

10. The apparatus of claim 1, wherein the XRD tube is housed wholly within the evacuable chamber.

11. The apparatus of claim 10, further comprising a cooling channel coupled from externally of the vacuum chamber to the XRD tube so as to supply cooling thereto, and a power connection also coupled from externally of the evacuable chamber to the XRD tube for supplying power thereto.

12. The apparatus of claim 11, wherein each of the cooling channel and the power connection is flexible along at least a part thereof so as to maintain power and cooling to the XRD tube as it moves relative to the evacuable chamber in use.

13. The apparatus of claim 1, wherein the XRD tube is arranged to generate a monochromatic x-ray beam whereas the XRF tube is arranged to generate a polychromatic x-ray beam.

* * * * *